(12) United States Patent
Hunke et al.

(10) Patent No.: US 8,354,041 B2
(45) Date of Patent: Jan. 15, 2013

(54) COMPOSITION AND PROCESS FOR WHITENING PAPER

(75) Inventors: Bernhard Hunke, Hennef (DE); Michael Kraemer, Kürten (DE); Andrei Tauber, Köln (DE); Günter Klug, Langenfeld (DE)

(73) Assignee: Blankophor GmbH & Co. KG (DE)

( * ) Notice: Subject to any disclaimer, the term of this patent is extended or adjusted under 35 U.S.C. 154(b) by 0 days.

(21) Appl. No.: 12/997,044

(22) PCT Filed: Jun. 10, 2009

(86) PCT No.: PCT/EP2009/057196
§ 371 (c)(1),
(2), (4) Date: Jan. 14, 2011

(87) PCT Pub. No.: WO2009/150180
PCT Pub. Date: Dec. 17, 2009

(65) Prior Publication Data
US 2011/0126996 A1    Jun. 2, 2011

(30) Foreign Application Priority Data

Jun. 11, 2008  (EP) .................................... 80105927

(51) Int. Cl.
*D21H 21/36*   (2006.01)
*C07D 251/00*  (2006.01)
*C09K 11/06*   (2006.01)

(52) U.S. Cl. ............... 252/301.23; 162/184; 106/213.1; 106/214.1; 106/217.1; 106/217.01

(58) Field of Classification Search ............... 162/184; 106/213.1, 214.1, 217.1, 217.01; 252/301.23
See application file for complete search history.

(56) References Cited

U.S. PATENT DOCUMENTS

| 3,272,805 | A | 9/1966 | Hausermann et al. |
| 4,466,900 | A * | 8/1984 | Horlacher et al. ....... 252/301.23 |
| 6,207,258 | B1 * | 3/2001 | Varnell .................. 428/32.1 |
| 2006/0065381 | A1 * | 3/2006 | Giesecke et al. ............ 162/162 |
| 2006/0252872 | A1 * | 11/2006 | Jonckheree ................ 524/493 |

FOREIGN PATENT DOCUMENTS

| GB | 1021527 | 3/1964 |
| GB | 1010759 | 9/1964 |
| WO | 9600220 | 1/1996 |
| WO | WO 96/00220 | * 1/1996 |
| WO | 03044275 A1 | 5/2003 |
| WO | 2004005617 A1 | 1/2004 |
| WO | 2005068597 | 7/2005 |
| WO | 2007048720 | 5/2007 |

OTHER PUBLICATIONS

International Preliminary Report on Patentability for International Application No. PCT/EP2009/057196; Date of Issuance of the Report: Dec. 14, 2010; 8 pages.
International Search Report and Written Opinion for International Application No. PCT/EP2009/057196; International Filing Date: Jun. 10, 2009; Mailing Date: Aug. 26, 2009; 10 pgs.

* cited by examiner

*Primary Examiner* — Carol M Koslow
(74) *Attorney, Agent, or Firm* — Cantor Colburn LLP (57) ABSTRACT

A composition suitable for surface treatment of paper, wherein the composition contains a specified fluorescent whitening agent with alkylsulfonic acid groups, a salt of a bivalent cation, and a carrier. The composition is used for whitening paper, in particular in the size press.

14 Claims, 3 Drawing Sheets

COMPOSITION AND PROCESS FOR WHITENING PAPER

CROSS REFERENCE TO RELATED APPLICATIONS

This is a U.S. national stage of application No. PCT/EP2009/057196, filed on 10 Jun. 2009. Priority under 35 U.S.C. §119(a) and 35 U.S.C. §365(b) is claimed from European Application No. 08010592.7, filed 11 Jun. 2008, the disclosure of which is also incorporated herein by reference.

BACKGROUND

The present invention relates to a composition suitable for surface treatment of paper, in particular a size press liquor, and a process for whitening paper using said composition.

In the production of paper, a sizing step is usually carried out for achieving good writing and printing properties and strength. Such a sizing step can take place, on the one hand, before the sheet formation in the paper pulp (internal sizing) and, on the other hand, after the sheet formation in the size press. A combination of both processes is also possible. In one or both production stages of paper, whitening of the pulp or of the paper sheet is usually also carried out by means of a fluorescent whitening agent (FWA). Usually, the size and fluorescent whitening agent are added separately to the paper pulp in the case of pulp application, whereas the fluorescent whitening agent is incorporated into the size press liquor and applied together with it to the paper sheet in the case of surface sizing.

The combination of surface sizing and whitening of papers is widely used in the paper-producing industry. This method is widely used particularly in the printing and writing paper segment (copy, inkjet, offset, etc.). There is a continuing trend towards surface-sized papers having high whiteness and improved printing performance and consequently there is a demand for size press liquors which are as effective as possible. U.S. Pat. No. 6,207,258 B1 discloses a composition and process for improved inkjet printing performance using a salt of a bivalent metal, in particular calcium chloride. Therefore, in order to achieve more brilliant and sharper printings, especially inkjet printings, the paper production industry uses nowadays calcium chloride in size press liquors. However, the use of that salt affects adversely the performance of the fluorescent whitening agents commonly used in size press liquors. In particular, the whitening effectiveness is decreased, the shade is moving to the greenish-yellowish direction, and additionally a loss of fluorescence is observed.

BRIEF SUMMARY

Surprisingly, it has been found that specific bis-triazinylamino-stilbene compounds containing alkylsulfonic acid groups when used in combination with salts of bivalent cations, such as calcium chloride, in compositions suitable for surface treating of paper, such as size press liquors, overcome problems of the prior art.

Therefore, the present invention relates to a composition suitable for surface treatment of paper, wherein the composition contains:

(a) at least one fluorescent whitening agent of formula (I)

wherein
m and n represent, independently of each other, an integer from 0 to 3;
$R_1$, $R_2$, $R_3$, $R_4$, $R_5$ and $R_6$ represent, independently of each other, hydrogen, cyano, $C_1$-$C_4$ alkyl, $C_1$-$C_4$ alkoxy, $C_1$-$C_4$ hydroxyalkyl, preferably $C_2$-$C_4$ hydroxyalkyl, wherein alkyl is linear or branched; or $R_3$ and $R_4$ or $R_5$ and $R_6$ independently of each other together with N atom form morpholine, piperidine or pyrrolidine ring; or —$(CH_2)_l$—$SO_3M$, wherein l is 1, 2 or 3; or wherein the —$SO_3M$ groups can be in o-, m- or p-position and k is an integer from 1 to 3; or —($C_1$-$C_4$ alkylene)—COOR, —($C_1$-$C_4$ alkylene)—CONHR, —($C_1$-$C_4$ alkylene)—COR, preferably —$(CH_2)_i$—COOR, —$(CH_2)_i$—CONHR, —$(CH_2)_i$—COR, wherein alkylene is linear or branched, i is an integer from 1 to 4, R is $C_1$-$C_3$ alkyl or equals to M;
M represents hydrogen, or one equivalent of a cation, in particular Li, Na, K, Ca, Mg, ammonium, or ammonium which is mono-, di-, tri- or tetra-substituted by $C_1$-$C_4$ alkyl or $C_2$-$C_4$ hydroxyalkyl;
(b) at least one salt of a bivalent cation;
(c) at least one carrier; and
(d) water.

The invention further relates to a process for whitening paper, wherein a cellulose sheet is brought into contact with the above defined composition, preferably in the size press.

Preferred embodiments of the invention are described in the description hereinafter, the claims and the figures.

DETAILED DESCRIPTION

In a preferred embodiment of the invention, the composition suitable for surface treatment of paper is a size press liquor, and the process is a process for whitening paper in the size press, wherein a cellulose sheet is brought into contact with the size press liquor.

In the context of this invention, size press is understood as meaning a surface application unit, preferably of the paper machine, in which the cellulose sheet formed is brought into contact with a size press liquor, and in which the proportion of the liquor which is to be taken up by the sheet (liquor absorption) can preferably be adjusted by means of the roll pressure.

Recent developments of the size press or film press, namely of the Speedsizer as well as of the Symsizer as well as Gateroll, are likewise understood as being covered by the term size press.

According to the invention the composition contains at least one bis-triazinylamino-stilbene compound of the above defined formula (I), wherein n, m, R1 to R6, and M are as defined above. In a preferred embodiment, n and m are integers from 1 to 2, most preferred 1. In another preferred embodiment, R1, R2, R3, R4, R5 and R6 represent, independently of each other, hydrogen, C1-C4 alkyl, C2-C4 hydroxyalkyl, wherein alkyl is linear or branched, —(CH$_2$)$_l$—SO$_3$M, l is 1, 2 or 3, or wherein the —SO$_3$M groups can be in o-, m-, or p-position and k is an integer from 1 to 3; more preferred n and m are 1. In a further preferred embodiment, R$_3$ and R$_5$ are both —CH$_2$CH$_2$SO$_3$M, wherein preferably n and m are 1. In another preferred embodiment, R$_1$, R$_2$, R$_4$ and R$_6$ are hydrogen and R$_3$ and R$_5$ are both —CH$_2$CH$_2$SO$_3$M, wherein preferably n and m are 1. In another preferred embodiment, R$_1$, R$_2$, R$_4$ and R$_6$ are hydrogen and R$_3$ and R$_5$ are both phenyl substituted with two —SO$_3$M groups in 2,5-position, wherein preferably n and m are 1. In another preferred embodiment, at least one of R$_1$, R$_2$, R$_4$ or R$_6$ is —(CH$_2$)$_1$SO$_3$M, 1 being 1, 2 or 3, and R$_3$ and R$_5$ are both —CH$_2$CH$_2$SO$_3$M.

Preferred embodiments of M are hydrogen, Na, K, Ca, Mg, in particular M is Na or K, most preferred is Na.

The fluorescent whitening agents of formula (I) can be produced according to known procedures. For example, GB 1,010,759 describes the preparation of such compounds. Generally, the compounds are prepared by reacting cyanuric chloride with 4,4'-diaminostilbene-2,2'-disulfonic acid or a salt thereof, and an appropriate sulfonic acid derivative, e.g. aminoalkane-sulfonic acid or a salt thereof.

The composition of the invention can contain more than one, preferably two or three, most preferred three, of the fluorescent whitening agents of formula (I).

Component (a) of the composition can contain, in addition to the at least one fluorescent whitening agent of formula (I), one or more known bis-triazinylamino-stilbene or distyrylbiphenyl based fluorescent whitening agents.

The salt of component (b) of the composition of the invention comprises bivalent cations, preferably cations of an earth alkaline metal, in particular calcium or magnesium. Preferably, the counterions of the bivalent cations are mono- or multivalent anions, in particular halide, sulphate, hydrosulphate, phosphate, hydrophosphate, dihydrophosphate, carbonate, hydrocarbonate, nitrate, acetate, or a mixture thereof, preferably chloride or sulphate, most preferably chloride. The salts disclosed in U.S. Pat. No. 6,207,258 B1 are also suitable. A preferred salt is calcium chloride, magnesium chloride, magnesium sulphate, or a mixture thereof; more preferred is calcium chloride, magnesium chloride, or a mixture thereof; most preferred is calcium chloride.

The carrier of component (c) is any compound known in the art to be suitable as a carrier, in particular carriers suitable for size press liquors. Preferred carriers are carboxymethylcellulose (CMC), polyvinyl alcohol (PVA), starch or mixtures thereof, with starch being particularly preferred. Suitable carrier substances are, for example, hydrophilic polymers having the ability to form hydrogen bridge bonds. Preferred carrier substances are starch, polyvinyl alcohols, carboxymethylcelluloses and polyethylene glycols having a number average molecular weight of from 200 to 8000 g/mol, as well as any desired mixtures of these substances, it being possible for these polymers optionally to be modified. Preferred polyvinyl alcohols are those having a degree of hydrolysis >85%, preferred carboxymethylcelluloses are those having a degree of substitution DS of >0.5. Polyethylene glycols having a number average molecular weight Mn of from 200 to 8000 g/mol are particularly preferred. Suitable starches are based e.g., but not exclusively, on potato starch, rice starch, wheat starch, maize starch or tapioca starch. In particular, starches whose molecular weights have already been reduced by partial degradation and/or which have been obtained by derivatization are preferably used instead of natural starches. Furthermore, starches for which both modification steps have been combined, i.e. which have been partially degraded and additionally derivatized, are suitable. Typical methods for starch degradation are, for example, enzymatic, oxidative, thermal or hydrolytic treatment. Examples of suitable starch derivatives are hydroxyethyl starch or cationic starch.

The composition of the invention contains as component (d) water and, optionally, can contain sizing agents, such as alkenyl ketene dimer, alkyl ketene dimer (AKD), alkenyl succinic anhydride (ASA), rosin size, styrene maleic anhydride copolymers, styrene acrylate, styrene acrylic acid copolymers, polyurethane or ethylene acrylic acid copolymers, or other common paper chemicals, such as styryl-acrylate copolymers, latex, pigments, defoamers, or salts, such as NaCl or NaHCO$_3$, or mixtures of two or more thereof.

The composition of the invention contains preferably component (a) in an amount of 0.02 to 3, more preferably 0.05 to 2, most preferably 0.1 to 1, weight-% based on 100 weight-% of the composition. If fluorescent whitening agents other than those of formula (I) are used, their amount is 5 to 95 weight-% based on 100 weight-% of component (a). Component (b) is preferably contained in an amount of 0.2 to 8, in particular 0.5 to 6, most preferably 1 to 5, weight-% based on 100 weight-% of the composition. Component (c) is preferably contained in an amount of 3 to 20, in particular 5 to 15, most preferably 6 to 12, weight-% based on 100 weight-% of the composition. The composition of the invention contains preferably water in an amount of 75 to 96.78, in particular 79 to 94.45, most preferably 82.5 to 92.9, weight-% based on 100 weight-% of the composition.

Optionally, the composition can contain sizing agent in an amount of 0 to 5, in particular 0 to 4, most preferably 0 to 3, in each case weight-% based on 100 weight-% of the composition.

In addition, relatively small amounts, usually amounts of less than 5% by weight, of further auxiliaries, such as, for example, dispersants, thickeners, antifreezes, preservatives, complexing agents, etc., or organic byproducts from the fluorescent whitening agent synthesis which were not completely removed in the working-up, may be contained in the composition of the invention.

Suitable compositions are also described in U.S. Pat. No. 6,207,258 B1, wherein according to the invention as component (a) at least one fluorescent whitening agent of formula (I) is used.

The production of the composition is effected by known methods and preferably effected by combining an aqueous solution of the fluorescent whitening agent used as component (a), which preferably has a suitable pH value, with the other components, such as carrier substances, sizing agents, binders, pigments, salts or standardizing agents. Preferably, an aqueous preparation of carrier component (c) is prepared, to which preparation an aqueous preparation of salt component (b) is added, followed by the addition of an aqueous preparation of the fluorescent whitening agent component (a), preferably adjusted in pH value, and the other components.

The process of the invention for whitening paper is carried out according to known processes, preferably using a size press, and is subject to no restrictions. The paper used is not critical and may be any cellulose sheet.

Paper obtained by the process of the invention exhibits, in addition to improved printing performance, improved whiteness, and is in particular suitable for inkjet printing applications.

The whiteness of the papers produced can be characterized by the CIE whiteness. Different fluorescent whitening agents can be compared to each other with respect to the saturation behavior when determined according to CIE whiteness. In other words, if a larger amount of fluorescent whitening agent is used and no further increase in whiteness is found, there is a saturation behavior and there may even be adverse effects on the whiteness when using higher amounts. The effect of saturation is also referred to as greening. The greening limit, i.e. the point at which increasing amounts of fluorescent whitening agent used results in virtually no further increase in whiteness, can be derived, for example, from the a*-b* diagram, where a* and b* are the color coordinates in the CIE-L*a*b system.

The following examples illustrate the invention and show preferred embodiments, without limiting the scope of protection.

EXAMPLES

Example 1

The whitening performance of different fluorescent whitening agents in the presence of calcium chloride was studied using the following test procedure for size press application.

First, a 15% starch solution of neutral oxidatively degraded potato starch (Perfectamyl 4692) and a 50% calcium chloride solution were prepared. The paper used was a 80 g/m² basepaper, which was a machine paper, internally sized (Cobb equals to 110 g/m²) and slightly whitened with fluorescent whitening agent to have the following optical characteristics: CIE-104.89; L*=93.92; a*=1.21; b*=−4.34.

The fluorescent whitening agent was weighed in a glass, and 13.33 g of 15% starch solution was added. Then, 50% calcium chloride solution was weighed in, and the solution was filled up with water to 20 g, so that the tests were carried out in a 10% starch solution. After stirring for a short time the solution was applied on one side of the basepaper by a semi-automatic lab coater with a Rakel (No. 2) which should simulate a film press application. 1.7 g/m2 of dry starch was applied on that basepaper. After the drawing the paper was directly dried on a drying cylinder at about 100° C. After climatization over night the prepared side of the papers were measured with a Datacolor spectrometer (ISO2469) by determining CIE, L*, a* and b*, the light source used based on ISO2469 standard.

The amounts used of fluorescent whitening agent per 100 g starch preparation were 0.28 g and 0.56 g, respectively; the amounts of calcium chloride were 0 and 2 g, respectively. The following fluorescent whitening agents were used:

FWA 1

The results obtained are summarized in Table 1.

TABLE 1

| FWA | Amount (wt %) in starch preparation CaCl₂ | Amount (wt %) in starch preparation FWA | CIE whiteness | L* | a* | b* | ΔCIE |
|---|---|---|---|---|---|---|---|
| FWA 1 | 0 | 0.28 | 126.13 | 93.66 | 2.42 | −9.15 | 1.93 |
|  | 2 | 0.28 | 128.06 | 93.72 | 2.42 | −9.56 |  |
|  | 0 | 0.56 | 132.94 | 93.84 | 2.66 | −10.59 | 0.11 |
|  | 2 | 0.56 | 133.05 | 94.03 | 2.37 | −10.53 |  |
| FWA 2 | 0 | 0.28 | 125.49 | 93.66 | 2.44 | −9.01 | 1.02 |
|  | 2 | 0.28 | 126.51 | 93.67 | 2.42 | −9.23 |  |
|  | 0 | 0.56 | 132.94 | 93.88 | 2.77 | −10.58 | −0.10 |

TABLE 1-continued

| FWA | Amount (wt %) in starch preparation CaCl$_2$ | FWA | CIE whiteness | L* | a* | b* | ΔCIE |
|---|---|---|---|---|---|---|---|
| | 2 | 0.56 | 132.84 | 93.95 | 2.59 | −10.52 | |
| Comparative 1 | 0 | 0.28 | 124.88 | 93.86 | 1.84 | −8.78 | −4.52 |
| | 2 | 0.28 | 120.36 | 93.95 | 0.94 | −7.74 | |
| | 0 | 0.56 | 127.34 | 94.18 | 1.31 | −9.18 | −7.68 |
| | 2 | 0.56 | 119.66 | 94.29 | −0.09 | −7.42 | |
| Comparative 2 | 0 | 0.28 | 127.95 | 93.74 | 2.30 | −9.52 | −0.85 |
| | 2 | 0.28 | 127.10 | 93.86 | 1.93 | −9.27 | |
| | 0 | 0.56 | 134.57 | 93.98 | 2.41 | −10.89 | −3.89 |
| | 2 | 0.56 | 130.68 | 94.16 | 1.61 | −9.93 | |
| Comparative 3 | 0 | 0.28 | 127.00 | 93.77 | 2.05 | −9.30 | −1.50 |
| | 2 | 0.28 | 125.50 | 94.00 | 1.37 | −8.86 | |
| | 0 | 0.56 | 134.21 | 94.13 | 2.06 | −10.74 | −8.61 |
| | 2 | 0.56 | 125.60 | 94.37 | 0.33 | −8.70 | |

Figure 1:
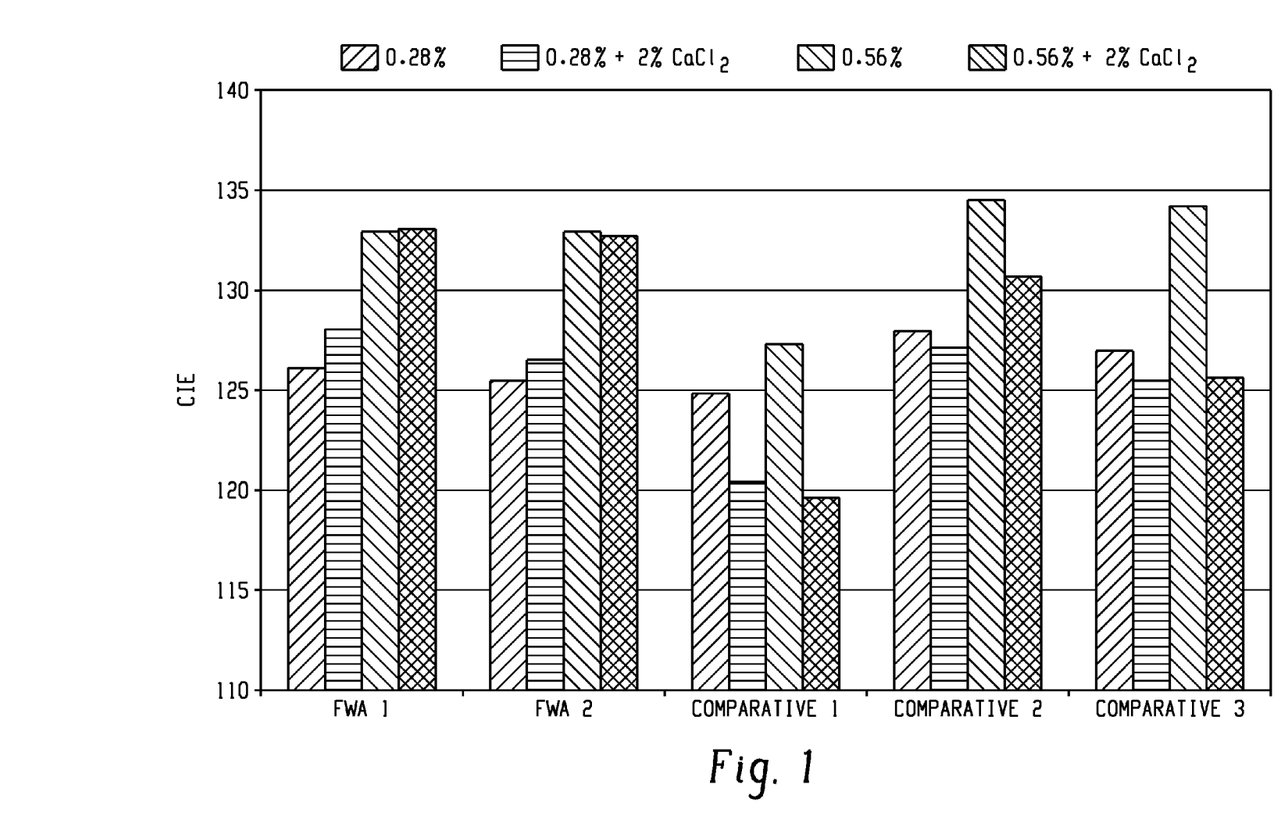
FIG. 1 is a diagram showing the influence of calcium chloride on the performance of different fluorescent whitening agents according to Example 1.

As may be taken from Table 1, FWA 1 and FWA 2 containing taurine groups, i.e. alkylsulfonic acid groups, according to the invention showed for almost all concentrations of fluorescent whitening agent used an improvement in whiteness (positive values for ΔCIE) by the presence of calcium chloride. This may be taken e.g. by a comparison of the values for 0.28 weight-% of FWA with and without calcium chloride. On the other hand, comparative FWAs 1 to 3 exhibited clear decreases in whiteness (negative values for ΔCIE). For further illustration, the results of Table 1 are also shown in the diagram of FIG. 1.

The above experimental data show that the use of bis-triazinylamino-stilbene fluorescent whitening agent compounds with alkylsulfonic acid groups, in particular taurine groups in the presence of a salt of a bivalent cation, such as calcium chloride, results in paper of improved whiteness.

Example 2

The whitening performance of a FWA of the invention and a comparative FWA has been studied in the presence of salts of the bivalent cations calcium, magnesium and barium (CaCl$_2$, MgCl$_2$ and BaCl2).

The test procedure was the same test procedure as used in Example 1. The amounts of the salts were 0 and 2 g, based on 100 g starch preparation, as indicated in Table 2 below. The amounts used of FWA were 0.28 g per 100 g starch preparation.

The FWA of the invention was FWA 3 which has the following formula:

For comparison, as FWA there was used Comparative 1 as described in Example 1.

Figure 2:
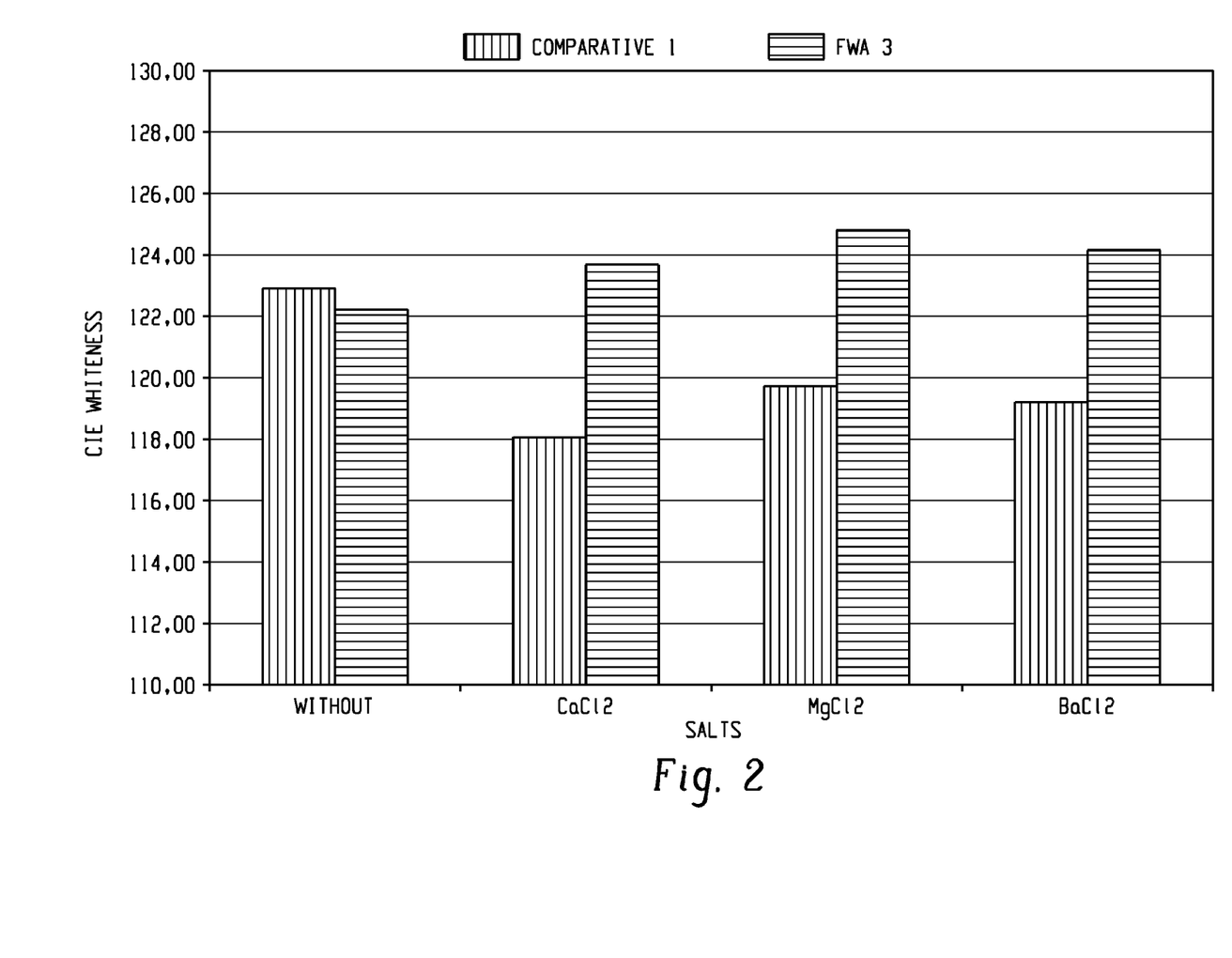
FIG. 2 is a diagram showing the effect of different salts of bivalent cations on the performance of different fluorescent whitening agents according to Example 2.

The results obtained are described in Table 2 below and further shown in FIG. 2.

TABLE 2

| FWA | Salt | Amount salt (wt %) in starch preparation | CIE whiteness | L* | a* | b* | ΔCIE |
|---|---|---|---|---|---|---|---|
| FWA 3 | — | 0 | 122.2 | 94.0 | 2.06 | −8.61 | |
| FWA 3 | CaCl$_2$ | 2 | 123.70 | 94.07 | 1.69 | −8.43 | 1.5 |
| | MgCl$_2$ | 2 | 124.77 | 94.00 | 1.88 | −8.70 | 2.57 |
| | BaCl$_2$ | 2 | 124.12 | 94.03 | 1.79 | −8.54 | 1.92 |
| Comparative 1 | — | 0 | 122.94 | 94.13 | 1.62 | −8.23 | |
| Comparative 1 | CaCl$_2$ | 2 | 118.07 | 94.18 | 0.70 | −7.12 | −4.87 |
| | MgCl$_2$ | 2 | 119.76 | 94.16 | 1.05 | −7.51 | −3.18 |
| | BaCl$_2$ | 2 | 119.18 | 94.17 | 0.96 | −7.38 | −3.76 |

The above experimental data evidence that the improved whitening in the presence of a salt of a bivalent cation is obtained with calcium chloride and other salts of bivalent cations.

Example 3

The whitening performance of different FWAs of the invention and Comparative FWAs in the presence of calcium chloride was studied. The test procedure was the same test procedure as used in Example 1. The amounts of calcium chloride were 0 and 2 g, based on 100 g starch preparation, as indicated in Table 3 below. The amounts used of FWA were 0.28 g, based on 100 g starch preparation, as also indicated in Table 3. The FWAs of the invention were FWA 1 and FWA 2 as described in Example 1, FWA 3 as described in Example 2, and further the following FWA 4:

FWA 3

FWA 4

For comparison, as FWAs there were used Comparative 1 and Comparative 2 as described in Example 1.

Figure 3:
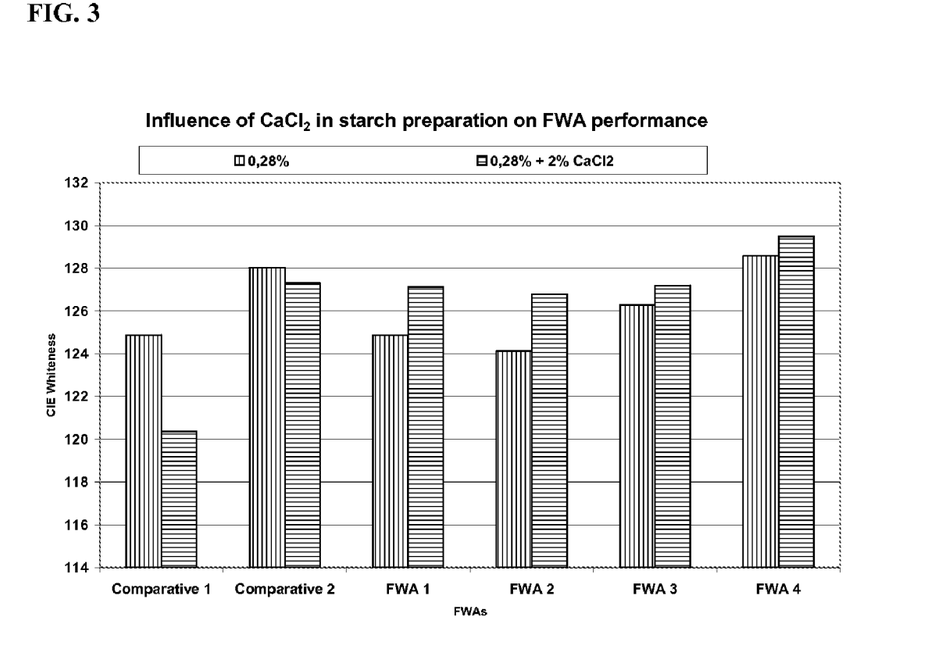
FIG. 3 is a further diagram showing the influence of calcium chloride on the performance of different fluorescent whitening agents according to Example 3.

The results obtained are described in Table 3 below and further shown in FIG. 3.

TABLE 3

| FWA | Amount (wt %) in starch preparation CaCl$_2$ | Amount (wt %) in starch preparation FWA | CIE whiteness | L* | a* | b* | ΔCIE |
|---|---|---|---|---|---|---|---|
| FWA 1 | 0 | 0.28 | 124.88 | 93.74 | 2.39 | −8.84 | 2.25 |
|  | 2 | 0.28 | 127.13 | 93.85 | 2.39 | −9.29 |  |
| FWA 2 | 0 | 0.28 | 124.13 | 93.66 | 2.43 | −8.71 | 2.64 |
|  | 2 | 0.28 | 126.77 | 93.79 | 2.45 | −9.24 |  |
| FWA 3 | 0 | 0.28 | 126.27 | 93.72 | 2.35 | −9.16 | 0.92 |
|  | 2 | 0.28 | 127.19 | 93.97 | 1.98 | −9.25 |  |
| FWA 4 | 0 | 0.28 | 128.58 | 93.80 | 2.50 | −9.64 | 0.90 |
|  | 2 | 0.28 | 129.48 | 93.89 | 2.43 | −9.80 |  |
| Comparative 1 | 0 | 0.28 | 124.88 | 93.86 | 1.84 | −8.78 | −4.52 |
|  | 2 | 0.28 | 120.36 | 93.95 | 0.94 | −7.74 |  |
| Comparative 2 | 0 | 0.28 | 128.02 | 93.82 | 2.31 | −9.50 | −0.72 |
|  | 2 | 0.28 | 127.30 | 93.96 | 1.91 | −9.28 |  |

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A composition suitable for surface treatment of paper, comprising:

(a) at least one fluorescent whitening agent of the formula (I)

wherein m and n represent, independently of each other, an integer from 0 to 3; $R_1$, $R_2$, $R_3$, $R_4$, $R_5$ and $R_6$ represent, independently of each other, hydrogen, cyano, $C_1$-$C_4$ alkyl, $C_1$-$C_4$ alkoxy, $C_1$-$C_4$ hydroxyalkyl, wherein the alkyl is linear or branched; or $R_3$ and $R_4$ or $R_5$ and $R_6$ independently of each other together with a N atom form a morpholine ring, a piperidine ring or a pyrrolidine ring; or —(CH$_2$)$_l$—SO$_3$M, wherein l is 1, 2 or 3; or wherein the —SO$_3$M groups can be in o-, m-, or p-position and k is an integer from 1 to 3; or —(C$_1$-C$_4$ alkylene)-COOR, —(C$_1$-C$_4$ alkylene)-CONHR, —(C$_1$-C$_4$ alkylene)-COR, wherein the alkylene is linear or branched, R is C$_1$-C$_3$ alkyl or M; wherein M represents hydrogen, or one equivalent of a cation selected from the group consisting of Li, Na, K, Ca, Mg, and ammonium, wherein the ammonium is mono-, di-, tri- or tetra-substituted by C$_1$-C$_4$ alkyl or C$_2$-C$_4$ hydroxyalkyl;

(b) at least one salt of a bivalent cation;

(c) at least one carrier; and (d) water, wherein the composition comprises component (a) in an amount of 0.02 to 3 weight-%, component (b) in an amount of 0.2 to 8 weight-%, and component (c) in an amount of 3 to 20 weight-%, each based on 100 weight-% of the composition.

2. The composition of claim 1, wherein n and m are 1, and $R_3$ and $R_5$ are —$CH_2CH_2SO_3M$.

3. The composition of claim 2, wherein $R_1$, $R_2$, $R_4$ and $R_6$ are hydrogen.

4. The composition of claim 1, wherein n and m are 1, $R_1$, $R_2$, $R_4$ and $R_6$ are hydrogen, and $R_3$ and $R_5$ are both phenyl substituted with two —$SO_3M$ groups at a 2,5-position.

5. The composition of claim 1, wherein $R_3$ and $R_5$ are —$CH_2CH_2SO_3M$, and at least one of $R_1$, $R_2$, $R_4$, or $R_6$ is —$(CH_2)_k$—$SO_3M$, wherein k is 1, 2 or 3.

6. The composition of claim 1, wherein M is Na or K.

7. The composition of claim 1, wherein the at least one salt of a bivalent cation of component (b) is calcium chloride.

8. The composition of claim 1, wherein the at least one carrier of component (c) is selected from the group consisting of carboxymethylcellulose, polyvinyl alcohol, starch, and mixtures thereof.

9. The composition of claim 8, wherein the at least one carrier is starch.

10. The composition of claim 1, wherein the composition is a size press liquor.

11. The composition of claim 10, wherein the composition further comprises a sizing agent.

12. A process for whitening paper, comprising contacting a cellulose sheet with the composition of claim 1.

13. The process of claim 12, wherein the contacting is conducted in a size press.

14. A paper obtainable by the process according to claim 12.

* * * * *